US00PP11987P2

(12) United States Plant Patent
Meier et al.

(10) Patent No.: US PP11,987 P2
(45) Date of Patent: Jul. 10, 2001

(54) KENTUCKY BLUEGRASS DESIGNATED 'BA75-173'

(75) Inventors: Virgil D. Meier, Marysville, OH (US); Jay B. Burr, Salem, OR (US)

(73) Assignee: OMS Investments, Inc., Wilmington, DE (US)

( * ) Notice: Subject to any disclaimer, the term of this patent is extended or adjusted under 35 U.S.C. 154(b) by 0 days.

(21) Appl. No.: 09/578,128

(22) Filed: May 24, 2000

(51) Int. Cl.[7] ..... A01H 5/00
(52) U.S. Cl. ..... Plt./393
(58) Field of Search ..... Plt./393

(56) References Cited

U.S. PATENT DOCUMENTS

| | | | |
|---|---|---|---|
| P.P. 3,150 | 5/1972 | Pepin et al. | Plt./393 |
| P.P. 3,156 | 5/1972 | Fuchigami et al. | Plt./393 |
| P.P. 3,186 | 5/1972 | Barenbrug et al. | Plt./393 |
| P.P. 4,336 | 11/1978 | Mayer et al. | Plt./393 |
| P.P. 6,280 | 9/1988 | Meier et al. | Plt./393 |
| P.P. 6,537 | 1/1989 | Meier et al. | Plt./393 |
| P.P. 6,538 | 1/1989 | Meier et al. | Plt./393 |
| P.P. 6,585 | 2/1989 | Meier et al. | Plt./393 |
| P.P. 7,831 | 3/1992 | Meier et al. | Plt./393 |
| P.P. 8,490 | 12/1993 | Meier et al. | Plt./393 |
| P.P. 9,036 | 1/1995 | Meier et al. | Plt./393 |
| P.P. 9,209 | 7/1995 | Meier et al. | Plt./393 |
| P.P. 9,611 | 7/1996 | Meier | Plt./393 |
| P.P. 9,848 | 4/1997 | Meier et al. | Plt./393 |
| P.P. 9,977 | 7/1997 | Meier et al. | Plt./393 |
| P.P. 10,080 | 10/1997 | Meier et al. | Plt./393 |
| P.P. 10,081 | 10/1997 | Meier et al. | Plt./393 |
| P.P. 10,384 | 5/1998 | Meier et al. | Plt./393 |

*Primary Examiner*—Annette H. Para
(74) *Attorney, Agent, or Firm*—Jones, Day, Reavis & Pogue

(57) ABSTRACT

A variety of Kentucky bluegrass having a high level of resistance to melting out, a medium to high level of resistance to summer patch, stem rust and grey snowmold, a medium to dark green color throughout the growing season; good fall color, good winter color during mild winters; the ability to form a good quality turf under a wide variety of environmental conditions; good seedling vigor making it competitive with *Poa annua*, and a high level of seed yielding capacity.

3 Drawing Sheets

BACKGROUND OF THE INVENTION

1. Field of the Invention

The present invention relates to a new and distinct variety of *Poa pratensis* that has been designated 'Ba75-173' Kentucky bluegrass.

2. Description of Related Art

Kentucky Bluegrasses have been disclosed in U.S. Plant Pat. No. 3,150, issued May 2, 1972; U.S. Plant Pat. No. 3,156, issued May 9, 1972, U.S. Plant Pat. No. 3,186, issued May 23, 1972; U.S. Plant Pat. No. 4,336, issued Nov. 28, 1978; U.S. Plant Pat. No. 6,280, issued Sep. 6, 1988; U.S. Plant Pat. Nos. 6,537 and 6,538, issued on Jan. 17, 1989; U.S. Plant Plant. No. 6,585, issued Feb. 7, 1989; U.S. Plant Pat. No. 7,831, issued Mar. 17, 1992; U.S. Plant Pat. No. 8,490, issued Dec. 7, 1993; U.S. Plant Pat. No. 9,036, issued Jan. 3, 1995; U.S. Plant Pat. No. 9,209, issued Jul. 18, 1995; U.S. Plant Pat. No. 9,611, issued Jul. 23, 1996; U.S. Plant Pat. No. 9,848, issued Apr. 1, 1997: U.S. Plant Pat. No. 9,977, issued Jul. 22, 1997; U.S. Plant Pat. No. 10,080, issued Oct. 21, 1997; U.S. Plant Pat. No. 10,081, issued Oct. 21, 1997; U.S. Plant Pat. No. 10,384, ussued May 5, 1998; U.S. Plant Pat. No. 10,925, issued May 25, 1999; and U.S. Plant Pat. No. 11,536, filed Feb. 27, 1998, U.S. Plant Pat. No. 11,520, filed Jul. 22, 1998 as well as U.S. Plant Pat. No. 11,647, filed Aug. 17, 1999.

SUMMARY OF THE VARIETY

'Ba75-173' plant material originated from a single plant that was progeny resulting from crossing 'Nugget' Kentucky Bluegrass, as the seed parent, with 'Ba70-46', an unreleased, unpatented Kentucky Bluegrass plant grown and maintained in a plant nursery in Marysville, Ohio, as the pollen parent. As a result of this breeding, a distinct variety was produced and asexually propagated by rhizomes, tillers and disseminules. The highly apomictic seed of 'Ba75-173' Kentucky bluegrass was produced first at Marysville, Ohio, and later at Gervais, Oreg. This seed was used to plant turf performance evaluation trials and later, seed production fields.

The seed of 'Ba75-173' has been found to be stable. Asexual production of 'Ba75-173' initially was performed at Marysville, Ohio by propagules (tillers and rhizomes) and by disseminules (modified caryopses produced by apomixis), and has consistently produced progeny plants indistinguishable from the first generation asexual reproductions of the instant plant. The apomixis level of 'Ba75-173' is approximately 98.4% (plus or minus 2.8%). The apomixis level was determined by examining seedling characteristics of approximately 100 to 150 seedlings from different crop years in a growth chamber and any seedling with one or more characteristics different from the other 'Ba75-173' seedlings was classified as not being of apomictic origin.

'Ba75-173' has a number of highly desirable characteristics, including a high level of resistance to Drechslera spp that causes melting out; a medium to high level of resistance to *Magnaporthe poae* that causes summer patch, a medium to high level of resistance to *Puccinia graminis* that causes stem rust, a medium to high level of resistance to *Sclerotinia homeocarpia* that causes dollarspot, and a medium to high level of resistance to Typhula spp that causes grey snowmold. 'Ba75-173' has an attractive leafy turf type and a medium to dark green color which can be maintained throughout the entire growing season. 'Ba75-173' demonstrates good fall color and good winter color under mild winter conditions.

'Ba75-173' is an overall good turfgrass performer as evidenced by good scores for quality and color throughout the cool season in turfgrass growing regions of the United States. 'Ba75-173' has a high seed yield potential in the bluegrass seed production region of the northwestern United States.

In comparison with other Kentucky bluegrass varieties, 'Ba75-173' has a larger seed (longer and wider) with a lower number of seeds per pound. The panicle of 'Ba75-173' Kentucky bluegrass is longer and has a higher number branches in the lowest whorl than other Kentucky bluegrasses. The peduncle is shorter and thicker, and the culm is longer than other Kentucky bluegrass varieties. It has a flag leaf that is wider and longer with a longer ligule that has more hairs when compared to other Kentucky bluegrasses.

DETAILED DESCRIPTION OF THE VARIETY

Figure 1:
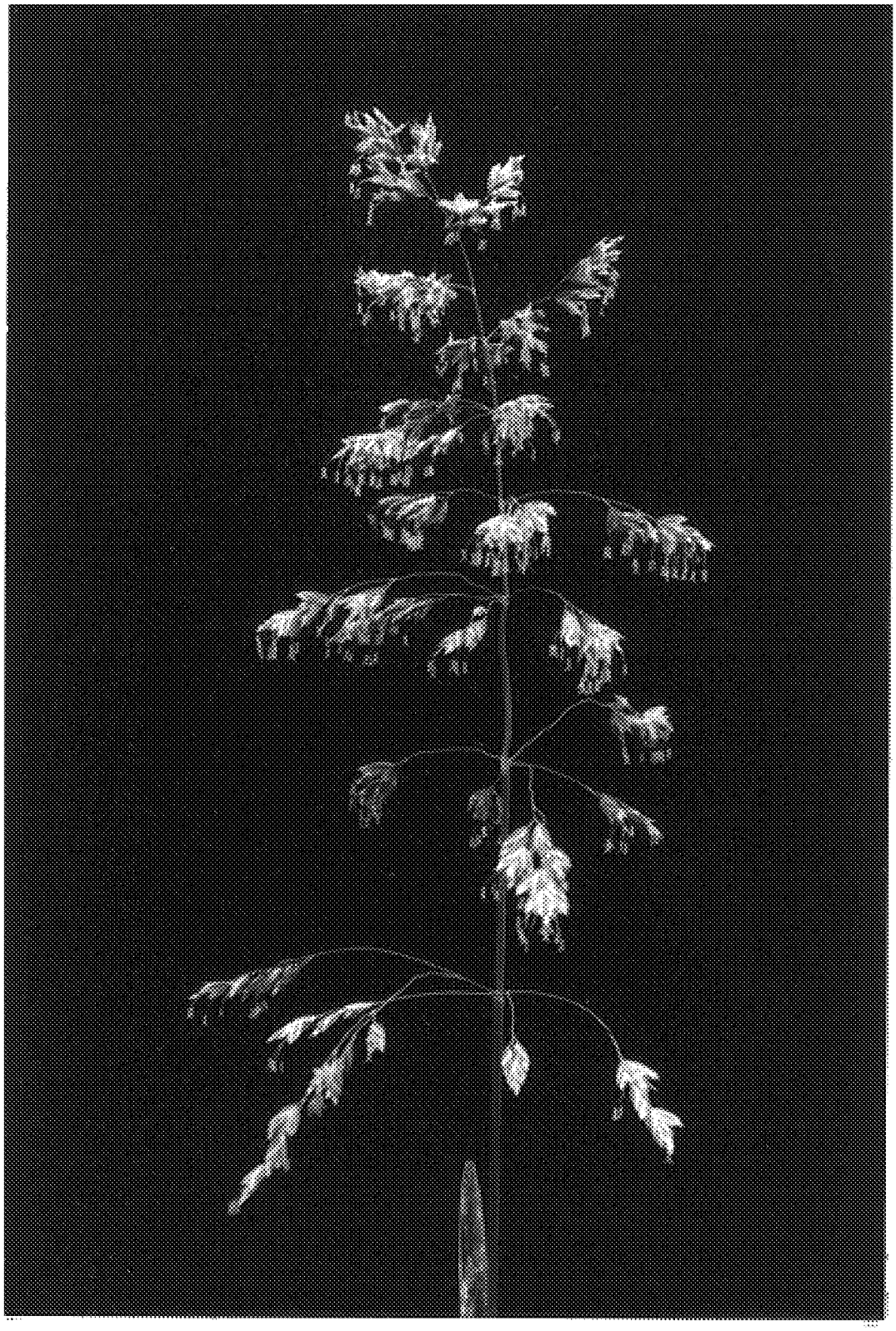
FIG. 1 is a 'Ba75-173' Kentucky bluegrass panicle.
Figure 2:
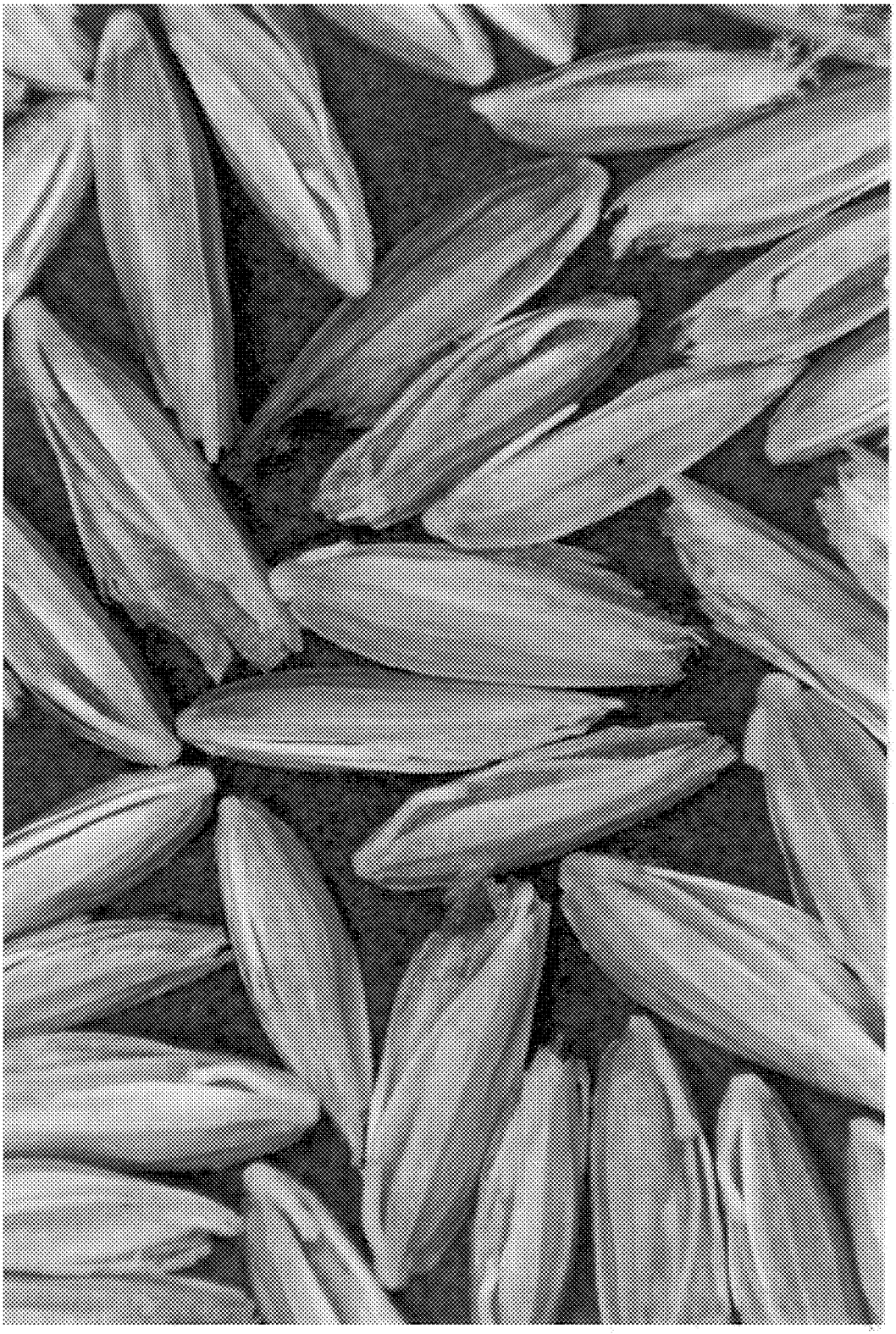
FIG. 2 is a 'Ba75-173' Kentucky bluegrass seed.
Figure 3:
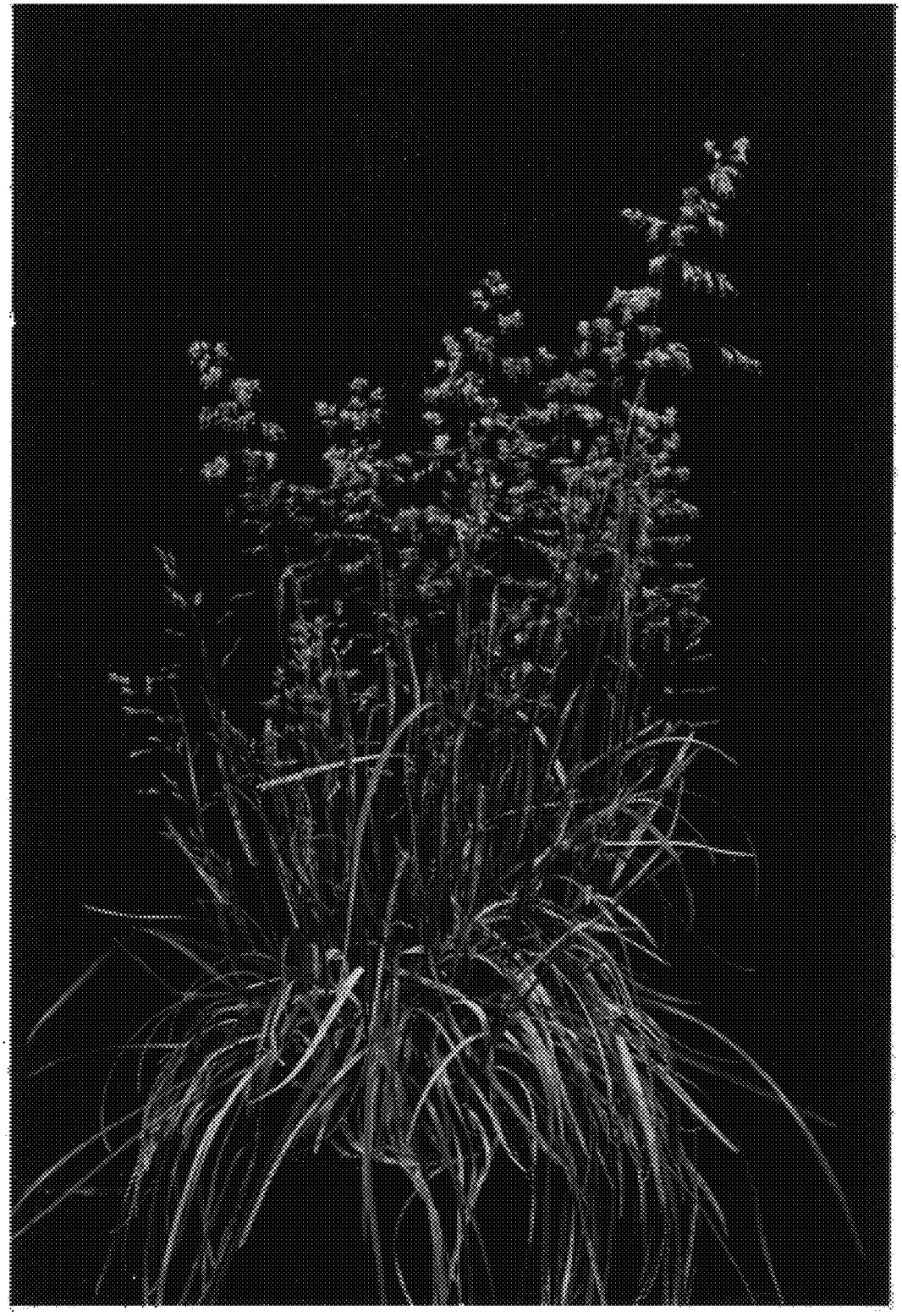
FIG. 3 is a 'Ba75-173' Kentucky bluegrass plant shortly after completing anthesis.

'Ba75-173' Kentucky bluegrass (*Poa pratensis* L.) is perennial with creeping rhizomes forming a dense turf. When plants overwinter in the field under freezing temperatures and are then brought into the greenhouse during late winter to continue growth undisturbed by clipping under moderate temperatures (60–80° F.), culms are erect averaging 45.7 cm in length. The uppermost internode averages 7.6 cm in length. The peduncle averages 20.8 cm in length and 0.90 mm in width. The vegetative leaf averages 26.9 cm in length, 3.7 mm in width, 0.28 mm in thickness and the ligule 0.34 mm in lenth. The flag leaf averages 6.1 cm in length, 3.8 mm in width, 0.27 mm in thickness and a ligule length of 1.13 mm.

The panicle averages 8.2 cm in length, 7.3 cm in width, and has 5.8 whorls. The lowest whorl and the third whorl from the bottom of the panicle average 4.4 and 3.5 branches, respectively. A spikelet in the lowest whorl averages 4.4 mm in length, 2.0 mm in width, 2.7 florets and the outer glume and inner glume average 2.8 mm and 3.2 mm in length, respectively. A spikelet from the third whorl from the bottom of the panicle averages 4.6 mm in length, 2.0 mm in width, 3.1 florets, and the outer glume and inner glume averages 2.8 mm and 3.3 mm in length, respectively. For the vegetative leaf, the number of hairs is about average for the leaf sheath margin, about average for the dorsal side of the leaf sheath, above average for the upper margin of the ligule, and about average for the collar margin. 'Ba75-173' differs from the other Kentucky bluegrass varieties in regard to such morphological characteristics as seed length and width, panicle length, number of branches in the lowest whorl, flag leaf length and width, flag leaf ligule length, flag leaf ligule hair, peduncle length and thickness, and culm length.

Since environmental conditions such as soil and climate may influence morphological characteristics to some extent, comparisons of 'Ba75-173' were made with other Kentucky bluegrass varieties under like conditions and the comparisons are set forth in Tables 1–7, as follows:

TABLE 1

Morphological Comparisons of Peduncles, Culms, Nodes, and Top Internodes of 'Ba75-173' with Other Kentucky Bluegrass Varieties in the Greenhouse at Marysville, Ohio.

| Variety | Peduncle Length (cm) | Peduncle Width (mm) | Culm Length (cm) | Number of Nodes | Top Internode Length (cm) |
|---|---|---|---|---|---|
| 'Ba75-173' | 20.78 | 0.90 | 45.7 | 2.9 | 7.57 |
| 'Abbey' | 23.20 | 0.87 | 45.1 | 3.0 | 7.44 |
| 'Ascot' | 21.17 | 0.73 | 40.6 | 2.2 | 6.54 |
| 'Coventry' | 22.54 | 0.79 | 42.8 | 2.6 | 8.22 |
| LSD (.05) | 2.39 | 0.09 | 2.8 | 0.4 | 1.56 |

TABLE 2

Morphological Comparisons of Vegetative Leaves of 'Ba75-173' and Other Kentucky Bluegrass Varieties in the Greenhouse at Marysville, Ohio.

| Variety | Length (cm) | Width (mm) | Thickness (mm) | Ligule Length (mm) |
|---|---|---|---|---|
| 'Ba75-173' | 26.94 | 3.71 | 0.276 | 0.34 |
| 'Abbey' | 29.39 | 3.70 | 0.303 | 0.33 |
| 'Ascot' | 25.19 | 3.61 | 0.288 | 0.29 |
| 'Coventry' | 29.92 | 3.18 | 0.267 | 0.24 |
| LSD (.05) | 3.69 | 0.37 | 0.037 | 0.04 |

TABLE 3

Morphological Comparisons of Flag Leaves of 'Ba75-173' and Other Kentucky Bluegrass Varieties in the Greenhouse at Marysville, Ohio.

| Variety | Length (cm) | Width (mm) | Thickness (mm) | Ligule Length (mm) | Ligule Hair* |
|---|---|---|---|---|---|
| 'Ba75-173' | 6.05 | 3.80 | 0.265 | 1.13 | 6.1 |
| 'Abbey' | 5.47 | 3.48 | 0.246 | 1.06 | 3.3 |
| 'Ascot' | 3.09 | 2.62 | 0.233 | 0.90 | 3.2 |
| 'Coventry' | 4.86 | 3.23 | 0.247 | 0.97 | 3.7 |
| LSD (.05) | 0.97 | 0.36 | 0.037 | 0.153 | 1.2 |

*Rating 0–9; 0 = none; 9 = many hairs.

TABLE 4

Morphological Comparisons for Panicle Length and Width, Whorl Number and Whorl Branches of 'Ba75-173' and Other Kentucky Bluegrass Varieties Grown in the Greenhouse in Marysville, Ohio.

| | Panicle | | | Number of Branches | |
|---|---|---|---|---|---|
| Variety | Length (cm) | Width (cm) | Whorl No. | Lowest Whorl | Third Whorl |
| 'Ba75-173' | 8.24 | 7.30 | 5.8 | 4.4 | 3.5 |
| 'Abbey' | 8.29 | 6.62 | 5.9 | 3.6 | 3.3 |
| 'Ascot' | 7.14 | 5.92 | 5.4 | 2.4 | 2.2 |
| 'Coventry' | 7.00 | 6.05 | 5.4 | 3.2 | 3.2 |
| LSD (.05) | 0.73 | 0.94 | 0.6 | 0.7 | 0.5 |

TABLE 5

Morphological Comparisons of Spikelets and Florets of 'Ba75-173' and Other Kentucky Bluegrass Varieties in the Greenhouse at Marysville, Ohio.

| | Spikelets | | | | No. of Florets | |
|---|---|---|---|---|---|---|
| | Lowest Whorl | | Third Whorl | | per Spikelet | |
| Variety | Length (mm) | Width (mm) | Length (mm) | Width (mm) | Lowest Whorl | Third Whorl |
| 'Ba75-173' | 4.38 | 1.96 | 4.55 | 2.01 | 2.7 | 3.1 |
| 'Abbey' | 4.50 | 1.88 | 4.78 | 2.04 | 2.0 | 3.4 |
| 'Ascot' | 4.45 | 1.67 | 4.58 | 1.97 | 1.7 | 2.7 |
| 'Coventry' | 4.70 | 1.93 | 4.69 | 1.77 | 3.2 | 3.5 |
| LSD (.05) | 0.52 | 0.30 | 0.49 | 0.38 | 0.6 | 0.6 |

TABLE 6

Morphological Comparisons of Glume Size of 'Ba75-173' and Other Kentucky Bluegrass Varieties in the Greenhouse at Marysville, Ohio.

| | Outer Glume Length (mm) | | Inner Glume Length (mm) | |
|---|---|---|---|---|
| Variety | Lowest Whorl | Third Whorl | Lowest Whorl | Third Whorl |
| 'Ba75-173' | 2.82 | 2.79 | 3.20 | 3.30 |
| 'Abbey' | 2.69 | 2.82 | 3.04 | 3.36 |
| 'Ascot' | 3.32 | 3.54 | 3.70 | 3.66 |
| 'Coventry' | 2.71 | 2.92 | 3.20 | 3.23 |
| LSD (.05) | 0.34 | 0.28 | 0.30 | 0.25 |

TABLE 7

Morphological Comparisons of the Level of Hairs on the Vegetative Leaves of 'Ba75-173' and Other Kentucky Bluegrass Varieties in the Greenhouse at Marysville, Ohio.*

| Variety | Leaf Sheath Margin | Ligule Upper Margin | Collar Margin | Leaf Sheath Dorsal |
|---|---|---|---|---|
| 'Ba75-173' | 0.5 | 3.3 | 3.3 | 1.4 |
| 'Abbey' | 0.1 | 3.0 | 3.0 | 2.1 |
| 'Ascot' | 0.7 | 2.6 | 4.8 | 0.8 |
| 'Coventry' | 1.2 | 3.5 | 3.6 | 1.4 |
| LSD (.05) | 0.6 | 0.5 | 0.7 | 0.7 |

*Rating Scale: 0–9; 0 = None; 9 = Many hairs.

The seed of 'Ba75-173' was conditioned by removing most of the extraneous materials that may have been harvested with the seed, such as small pieces of plant stems and leaves, soil particles, seed of other plants, hair attached to the seed and the like. This conditioned seed of 'Ba75-173' averages 3.20 mm in length, and 0.87 mm in width. 'Ba75-173' has about 860,930 seeds per pound.

Comparisons of 'Ba75-173' with other Kentucky bluegrass varieties in terms of seed numbers per pound and other seed characteristics are shown in Tables 8–9 as follows:

TABLE 8

Morphological Comparisons of Conditioned Seed of 'Ba75-173' and Other Kentucky Bluegrass Varieties.*

| Variety | Length (mm) | Width (mm) |
|---|---|---|
| 'Ba75-173' | 3.20 | 0.88 |
| 'Abbey' | 2.99 | 0.84 |
| 'Ascot' | 3.19 | 0.82 |
| 'Coventry' | 2.62 | 0.77 |
| LSD (.05) | 0.16 | 0.06 |

*Rating Scale 0–9; 9 = most hairs

TABLE 9

Comparison of Seeds Per Pound of 'Ba75-173' and Other Kentucky Bluegrass Varieties After Conditioning.

| Variety | Seeds per Pound |
|---|---|
| 'Ba75-173' | 860,930 |
| 'Abbey' | 1,003,000 |
| 'Ascot' | 1,039,400 |
| 'Coventry' | 1,374,700 |
| 'Famous' | 1,127,500 |
| 'Goldrush' | 942,700 |
| 'Misty' | 1,126,400 |
| 'Nottingham' | 1,071,300 |
| 'Raven' | 1,001,400 |
| 'Sidekick' | 987,300 |
| LSD (.05) | 38,080 |

'Ba75-173' has performed well throughout the U.S. as exhibited by good turf quality ratings in both the sun and shade in comparison with other Kentucky bluegrass varieties. In addition, it has a medium to dark green color which can be maintained throughout the growing season, good seedling vigor making it very competitive with the weed *Poa annua*, and a high seed yielding capacity.

With regard to a comparative analysis conducted for purposes of determining color of 'Ba75-173' plants relative to other Kentucky bluegrass varieties, readings were taken of the vegetative color of 'Ba75-173' during mid-October while the turf was actively growing with adequate nutrient and water availability. The readings were taken in full sun with several actively growing leaves being compared, one at a time, utilizing color chips from the Munsell Book of Color as a reference. On this basis, the color of 'Ba75-173' was determined to be 5 GY 4/4. During the same time period, the color of similar leaves of other Kentucky bluegrass varieties were determined by the same procedure to be as follows: 'Ascot'—5 GY 4/4; 'Buckingham'—7.5 GY 4/4; 'Nottingham'—5 GY 4/6; 'Midnight'—7.5 GY 4/4; 'Abbey'—5 GY 4/6; and 'Victa'—5 GY 4/4. However, it should be noted that the general apparent color of turf does not always correlate directly with the color of the individual actively growing leaves within the turf and that turf color varies with nutrient level and time of year with some varieties being darker of lighter green, depending on such factors.

Comparisons of 'Ba75-173' with other Kentucky bluegrass varieties for quality, genetic color, fall color, winter color, turf density, leaf texture, seedling vigor, level of *Poa annua* in seedling turf, and seed yeild are set forth hereinafter in Tables 10–17 as follows:

TABLE 10

A Comparison of Quality of 'Ba75-173' and Other Kentucky Bluegrass Varieties as Affected by Environmental Conditions.

| Variety | Shade[1] | Sun[2] |
|---|---|---|
| 'Ba75-173' | 5.1 | 5.7 |
| 'Abbey' | 4.2 | 5.7 |
| 'Allure' | 5.4 | 6.2 |
| 'America' | 5.3 | 6.4 |
| 'Ascot' | 5.4 | 5.9 |
| 'Baron' | 3.7 | 5.8 |
| 'Blacksburg' | 3.6 | 6.4 |
| 'Challenger' | 4.5 | 6.1 |
| 'Chateau' | 5.3 | 6.1 |
| 'Classic' | 4.7 | 5.8 |
| 'Coventry' | 5.1 | 6.1 |
| 'Eclipse | 4.6 | 6.1 |
| 'Glade' | 4.4 | 6.1 |
| 'Goldrush' | 4.7 | 5.8 |
| 'Haga | 5.0 | 6.0 |
| 'Kenblue | 3.2 | 4.6 |
| 'Limousine' | 4.8 | 6.2 |
| 'Midnight' | 3.2 | 6.6 |
| 'Misty' | 4.4 | 5.7 |
| 'Raven' | 3.4 | 5.8 |
| 'Sebring' | 4.7 | 6.0 |
| 'Sidekick' | 4.3 | 5.3 |
| 'Unique' | 5.3 | 6.4 |
| LSD (.05) | 1.6 | 0.2 |

Rating Scale: 0–9; 9 = Excellent.
[1]From Maryland
[2]From 28 different locations in the US

TABLE 11

A Comparison of Quality of 'Ba75-173' and Other Kentucky Bluegrass Varieties as Affected by Climatic Regions in the U.S.

| Variety | Transition Zone[1] | Cool Humid[2] | Cool Arid[3] |
|---|---|---|---|
| 'Ba75-173' | 5.4 | 5.5 | 6.3 |
| 'Abbey' | 5.4 | 5.6 | 6.2 |
| 'Allure' | 5.6 | 5.9 | 6.2 |
| 'America' | 6.2 | 6.5 | 6.5 |
| 'Ascot' | 5.4 | 5.8 | 6.4 |
| 'Baron' | 5.3 | 5.6 | 6.6 |
| 'Blacksburg' | 5.9 | 6.1 | 6.6 |
| 'Challenger' | 5.6 | 5.7 | 6.5 |
| 'Chateau' | 5.6 | 6.0 | 6.2 |
| 'Classic' | 5.3 | 5.7 | 5.8 |
| 'Coventry' | 5.6 | 6.0 | 5.9 |
| 'Eclipse' | 5.8 | 6.0 | 6.1 |
| 'Glade' | 5.9 | 6.0 | 6.8 |
| 'Goldrush' | 5.7 | 5.4 | 6.3 |
| 'Haga' | 5.5 | 5.6 | 5.9 |
| 'Kenblue' | 4.4 | 4.6 | 5.0 |
| 'Limousine' | 5.3 | 6.2 | 5.9 |
| 'Midnight' | 6.6 | 6.4 | 7.3 |
| 'Misty' | 4.8 | 5.7 | 6.1 |
| 'Raven' | 5.4 | 5.7 | 6.1 |
| 'Sebring' | 5.4 | 5.9 | 6.4 |
| 'Sidekick' | 5.3 | 5.3 | 5.8 |
| 'Unique' | 6.5 | 6.3 | 6.7 |
| LSD VALUE | 0.3 | 0.2 | 0.3 |

Rating Scale: 0–9; 9 = Excellent.
[1]From 9 different locations in the U.S.
[2]From 3 different locations in the U.S.
[3]From 15 different locations in the U.S.

TABLE 12

A Comparison of Genetic Color, Fall Color and Winter Color of 'Ba75-173' and Other Kentucky Bluegrass Varieties.

| Variety | Genetic Color[1] | Fall Color[2] | Winter Color[3] |
|---|---|---|---|
| 'Ba75-173' | 6.7 | 5.7 | 5.5 |
| 'Abbey' | 6.4 | 4.7 | 5.0 |
| 'Allure' | 6.2 | 4.0 | 4.3 |
| 'America' | 6.7 | 4.3 | 5.7 |
| 'Ascot' | 6.8 | 4.0 | 4.5 |
| 'Baron' | 6.6 | 4.7 | 5.2 |
| 'Blacksburg' | 7.1 | 5.3 | 5.7 |
| 'Challenger' | 6.7 | 4.7 | 6.2 |
| 'Chateau' | 6.1 | 4.7 | 5.0 |
| 'Classic' | 6.1 | 4.3 | 6.0 |
| 'Coventry' | 6.2 | 4.7 | 4.7 |
| 'Eclipse' | 6.4 | 4.3 | 5.3 |
| 'Glade' | 7.3 | 4.7 | 5.3 |
| 'Goldrush' | 6.5 | 4.3 | 4.8 |
| 'Haga' | 5.9 | 4.7 | 5.8 |
| 'Kenblue' | 5.5 | 3.7 | 5.3 |
| 'Limousine' | 5.7 | 4.0 | 4.3 |
| 'Midnight' | 7.7 | 5.3 | 5.7 |
| 'Misty' | 6.4 | 4.3 | 5.8 |
| 'Raven' | 6.5 | 5.0 | 4.5 |
| 'Sebring' | 7.4 | 4.3 | 5.8 |
| 'Sidekick' | 6.3 | 4.0 | 5.2 |
| 'Unique' | 6.4 | 4.3 | 6.3 |
| LSD VALUE | 0.2 | 1.2 | 0.8 |

Rating 1–9; 9 = Dark Green.
[1]From 24 different locations in the U.S.
[2]From 1 location in the U.S.
[3]From 2 different locations in the U.S.

TABLE 13

A Comparison of Turf Density of 'Ba75-173' and Other Kentucky Bluegrass Varieties.

| | Turf Density | | |
|---|---|---|---|
| Variety | Spring[1] | Summer[2] | Fall[3] |
| 'Ba75-173' | 6.9 | 6.8 | 6.9 |
| 'Abbey' | 6.8 | 6.7 | 6.7 |
| 'Allure' | 7.5 | 6.9 | 7.0 |
| 'America' | 7.0 | 7.0 | 7.3 |
| 'Ascot' | 7.2 | 6.8 | 7.1 |
| 'Baron' | 6.9 | 6.7 | 6.8 |
| 'Blacksburg' | 7.2 | 7.4 | 7.4 |
| 'Challenger' | 7.0 | 6.8 | 6.8 |
| 'Chateau' | 7.7 | 6.8 | 7.1 |
| 'Classic' | 7.1 | 6.4 | 6.7 |
| 'Coventry' | 7.4 | 6.8 | 6.8 |
| 'Eclipse' | 7.0 | 6.5 | 7.1 |
| 'Glade' | 7.1 | 7.2 | 7.1 |
| 'Goldrush' | 7.1 | 6.9 | 6.8 |
| 'Haga' | 7.2 | 6.6 | 6.9 |
| 'Kenblue' | 5.9 | 6.3 | 6.5 |
| 'Limousine' | 7.6 | 7.8 | 7.6 |
| 'Midnight' | 7.5 | 7.4 | 7.4 |
| 'Misty' | 7.0 | 6.8 | 7.1 |
| 'Raven' | 7.1 | 6.6 | 6.8 |
| 'Sebring' | 6.7 | 6.8 | 6.8 |
| 'Sidekick' | 6.8 | 6.4 | 6.5 |
| 'Unique' | 7.2 | 7.0 | 7.5 |
| LSD VALUE | 0.5 | 0.3 | 0.4 |

Density Rating 1–9; 9 = maximum density.
[1]From 8 different locations in the U.S.
[2]From 9 different locations in the U.S.
[3]From 12 different locations in the U.S.

TABLE 14

A Comparison of Leaf Texture of 'Ba75-173' and Other Kentucky Bluegrass Varieties.

| Variety | Leaf Texture[1] |
|---|---|
| 'Ba75-173' | 5.5 |
| 'Abbey' | 5.5 |
| 'Allure' | 5.8 |
| 'America' | 6.7 |
| 'Ascot' | 6.0 |
| 'Baron' | 5.7 |
| 'Blacksburg' | 6.3 |
| 'Challenger' | 6.2 |
| 'Chateau' | 5.7 |
| 'Classic' | 6.2 |
| 'Coventry' | 5.6 |
| 'Eclipse' | 6.0 |
| 'Glade' | 6.5 |
| 'Goldrush' | 6.0 |
| 'Haga' | 6.4 |
| 'Kenblue' | 6.9 |
| 'Limousine' | 7.0 |
| 'Midnight' | 6.4 |
| 'Misty' | 5.2 |
| 'Raven' | 5.6 |
| 'Sebring' | 6.0 |
| 'Sidekick' | 5.1 |
| 'Unique' | 6.8 |
| LSD VALUE | 0.3 |

Texture Rating 1–9; 9 = fine texture.
[1]From 24 different locations in the U.S.

TABLE 15

A Comparison of Seedling Vigor and Level of *Poa annua* in New Seedlings of 'Ba75-173' and Other Kentucky Bluegrass Varieties.

| Variety | Seedling Vigor[1] | *Poa Annua* Level[2] |
|---|---|---|
| 'Ba75-173' | 5.1 | 7.0 |
| 'Abbey' | 5.1 | 7.0 |
| 'Allure' | 4.9 | 5.3 |
| 'America' | 5.6 | 7.7 |
| 'Ascot' | 4.8 | 4.3 |
| 'Baron' | 5.2 | 7.0 |
| 'Blacksburg' | 5.1 | 6.7 |
| 'Challenger' | 5.0 | 5.0 |
| 'Chateau' | 5.2 | 5.3 |
| 'Classic' | 5.7 | 7.7 |
| 'Coventry' | 4.9 | 6.3 |
| 'Eclipse' | 4.8 | 5.0 |
| 'Glade' | 5.3 | 6.3 |
| 'Goldrush' | 4.9 | 6.0 |
| 'Haga' | 6.3 | 7.3 |
| 'Kenblue' | 6.4 | 7.7 |
| 'Limousine' | 5.1 | 6.0 |
| 'Midnight' | 5.1 | 6.0 |
| 'Misty' | 4.5 | 3.0 |
| 'Raven' | 5.2 | 6.3 |
| 'Sebring' | 5.0 | 4.7 |
| 'Sidekick' | 4.7 | 5.3 |
| 'Unique' | 5.3 | 6.3 |
| LSD VALUE | 0.3 | 1.5 |

Ratings: 1–9; 9 = better seedling vigor and less *Poa annua*.
[1]From 24 different locations in the U.S.
[2]From 1 location in the U.S.

TABLE 16

A Comparison of Seed Yield (Pounds per Acre) of 'Ba75-173' and Other Kentucky Bluegrass Varieties in Four (4) Tests Conducted at Gervais, Oregon.

| Variety | Test 1 Yield (bs./A) | Test 2 Yield (bs./A) | Test 3 Yield (bs./A) | Test 4 Yield (bs./A) |
|---|---|---|---|---|
| 'Ba75-173' | 809 | 868 | 350 | 209 |
| 'Abbey' | 516 | 848 | 483 | 249 |
| 'Buckingham' | 457 | 1071 | 555 | 328 |
| 'Coventry' | 480 | 429 | 111 | 268 |
| 'Goldrush' | 514 | 785 | 341 | 214 |
| 'Midnight' | 112 | 618 | 251 | 233 |
| 'Misty' | 913 | 890 | 291 | 220 |
| 'Sidekick' | 1196 | 982 | 673 | 638 |
| LSD (.05) | 100 | 130 | 81 | 59 |

TABLE 17

A Comparison of Seed Yield (Pounds per Acre) of 'Ba75-173' and Other Kentucky Bluegrass Varieties in Two (2) Tests Conducted at Imbler, Oregon.

| Variety | Test 1 Yield (lbs./A) | Test 2 Yield (lbs./A) |
|---|---|---|
| 'Ba75-173' | 1385 | 924 |
| 'Abbey' | 1484 | 1003 |
| 'Coventry' | 915 | 586 |
| 'Goldrush' | 1165 | 865 |
| 'Misty' | 1193 | 799 |
| 'Sebring' | 1182 | 610 |
| LSD (.05) | 200.6 | 144.9 |

Turf diseases are one of the major causes of inconsistent and poor turf performance. 'Ba75-173' has been found to have a medium to high level of resistance to melting out caused by *Drechslera poae* (formerly called *Helminthosporium vagans*); a medium to high level of resistance to summer patch caused by *Magnaporthe poae*, a medium to high level of resistance to stem rust caused by *Puccinia graminis*, a medium to high level of resistance to dollarspot caused by *Sclerotinia homeocarpia*, and a medium to high level of resistance to grey snowmold caused by Typhula ssp.

Comparisons of disease incidence of 'Ba75-173' as compared with other Kentucky bluegrass varieties in regard to melting out, summer patch, stem rust, dollarspot, and grey snowmold are presented in Table 18 as follows:

TABLE 18

A Comparison of Diseases of 'Ba75-173' and Other Kentucky Bluegrass Varieties.

| Variety | Melting Out[1] | Summer Patch[2] | Stem Rust[3] | Dollarspot[4] | Snowmold[5] |
|---|---|---|---|---|---|
| 'Ba75-173' | 9.0 | 9.0 | 8.0 | 8.2 | 7.3 |
| 'Abbey' | 9.0 | 8.7 | 7.3 | 8.0 | 7.3 |
| 'Allure' | 7.0 | 8.3 | 5.7 | 6.8 | 7.0 |
| 'America' | 8.3 | 9.0 | 7.7 | 8.8 | 7.7 |
| 'Ascot' | 8.7 | 6.3 | 5.7 | 8.7 | 7.0 |
| 'Baron' | 9.0 | 7.0 | 7.3 | 7.9 | 6.7 |
| 'Blacksburg' | 6.3 | 9.0 | 7.7 | 7.3 | 6.0 |
| 'Challenger' | 9.0 | 8.7 | 6.7 | 7.6 | 8.0 |
| 'Chateau' | 8.0 | 7.3 | 7.3 | 6.1 | 7.3 |
| 'Classic' | 7.0 | 9.0 | 6.0 | 7.7 | 7.0 |
| 'Coventry' | 7.3 | 8.7 | 6.3 | 7.3 | 7.3 |
| 'Eclipse' | 9.0 | 9.0 | 6.7 | 7.7 | 7.3 |

TABLE 18-continued

A Comparison of Diseases of 'Ba75-173' and Other Kentucky Bluegrass Varieties.

| Variety | Melting Out[1] | Summer Patch[2] | Stem Rust[3] | Dollarspot[4] | Snowmold[5] |
|---|---|---|---|---|---|
| 'Glade' | 5.0 | 9.0 | 6.3 | 7.6 | 7.0 |
| 'Goldrush' | 9.0 | 8.0 | 6.3 | 8.2 | 7.7 |
| 'Haga' | 7.7 | 8.7 | 7.0 | 7.9 | 7.0 |
| 'Kenblue' | 1.3 | 6.7 | 3.7 | 6.7 | 6.7 |
| 'Limousine' | 9.0 | 9.0 | 7.0 | 6.4 | 7.3 |
| 'Midnight' | 9.0 | 8.3 | 7.7 | 8.2 | 7.0 |
| 'Misty' | 7.3 | 8.0 | 5.3 | 8.3 | 7.3 |
| 'Raven' | 9.0 | 8.7 | 4.7 | 7.2 | 7.0 |
| 'Sebring' | 9.0 | 9.0 | 5.7 | 7.0 | 7.7 |
| 'Sidekick' | 7.0 | 9.0 | 6.0 | 8.6 | 6.3 |

TABLE 18-continued

A Comparison of Diseases of 'Ba75-173' and Other Kentucky Bluegrass Varieties.

| Variety | Melting Out[1] | Summer Patch[2] | Stem Rust[3] | Dollarspot[4] | Snowmold[5] |
|---|---|---|---|---|---|
| 'Unique' | 8.7 | 9.0 | 7.7 | 8.4 | 7.3 |
| LSD VALUE | 1.3 | 1.6 | 3.4 | 1.0 | 1.5 |

Rating Scale: 1–9; 9 = No Disease.
[1]From Pennsylvania
[2]From Indiana
[3]From North Carolina
[4]From 3 locations in the USA
[5]From Quebec

What is claimed is:

1. A new and distinct variety of Kentucky bluegrass plant, as herein illustrated and described.

* * * * *